United States Patent
Talmaki et al.

(10) Patent No.: US 9,989,511 B2
(45) Date of Patent: Jun. 5, 2018

(54) AUTOMATED MATERIAL TAGGING SYSTEM

(71) Applicant: Caterpillar Inc., Peoria, IL (US)

(72) Inventors: Sanat Arun Talmaki, Plainfield, IL (US); Jason Louis Smallenberger, Morton, IL (US)

(73) Assignee: Caterpillar Inc., Deerfield, IL (US)

( * ) Notice: Subject to any disclaimer, the term of this patent is extended or adjusted under 35 U.S.C. 154(b) by 495 days.

(21) Appl. No.: 14/683,644

(22) Filed: Apr. 10, 2015

(65) Prior Publication Data
US 2016/0299116 A1 Oct. 13, 2016

(51) Int. Cl.
| | |
|---|---|
| *G01V 3/38* | (2006.01) |
| *G01N 33/24* | (2006.01) |
| *G01S 19/42* | (2010.01) |
| *E21C 41/26* | (2006.01) |
| *G01S 5/02* | (2010.01) |

(52) U.S. Cl.
CPC .............. *G01N 33/24* (2013.01); *E21C 41/26* (2013.01); *G01S 5/02* (2013.01); *G01S 5/0247* (2013.01); *G01S 19/42* (2013.01)

(58) Field of Classification Search
CPC ...... C09D 163/00; C09D 5/00; C09D 11/037; C09D 11/033; C09D 11/10; C09D 11/103; C09D 11/104; C09D 161/28; C09D 197/02; C09D 7/1283; G21K 1/08; G21K 5/04; B22F 2003/1057; B22F 3/1055

See application file for complete search history.

(56) References Cited

U.S. PATENT DOCUMENTS

| | | | |
|---|---|---|---|
| 5,850,341 A | 12/1998 | Fournier et al. | |
| 6,114,993 A | 9/2000 | Henderson et al. | |
| 6,741,921 B2 | 5/2004 | Cohen et al. | |
| 7,401,054 B1 * | 7/2008 | Shah ................. | G06F 17/30607 705/51 |
| 8,958,905 B2 * | 2/2015 | Bamber .................. | B07C 5/344 37/443 |
| 9,487,931 B2 * | 11/2016 | Atkinson ................. | E02F 3/432 |
| 2006/0206623 A1 * | 9/2006 | Gipps .................... | G06Q 10/04 709/238 |
| 2013/0272829 A1 * | 10/2013 | Innes ..................... | G01G 19/08 414/399 |
| 2014/0180547 A1 | 6/2014 | Edara et al. | |

* cited by examiner

*Primary Examiner* — Roy Y Yi
(74) *Attorney, Agent, or Firm* — Finnegan, Henderson, Farabow, Garrett & Dunner, LLP; James S. Bennin

(57) ABSTRACT

A material tagging system is disclosed for use with an excavation machine. The material tagging system may have a locating device configured to generate a first signal indicative of a location of the excavation machine at a worksite, and a communication device. The material tagging system may also have at least one of an operator input device and a sensor configured to generate a second signal indicative of an identity of material in a work tool, and a controller. The controller may be configured to receive an electronic map of the worksite predicting locations of different types of material, and to make a comparison of the identity of the material with a type of material predicted to be at a location where the excavation machine was located when the material was loaded. The controller may further be configured to selectively generate and communicate an error flag based on the comparison.

20 Claims, 3 Drawing Sheets

AUTOMATED MATERIAL TAGGING SYSTEM

TECHNICAL FIELD

The present disclosure relates generally to a material tagging system and, more particularly, to an automated material tagging system.

BACKGROUND

Material tagging is a known mining-related process, wherein an electronic map or digital model of a mining area is created (e.g., based on core sampling, arial photography, and/or surveying). The map or model includes contours of the mining area, along with an identification of three-dimensional boundaries of ore seams within the area. The different ore seams can be categorized based on type, size, quality, concentration, value, accessibility, etc., and excavation plans can be created that use the categories to accomplish a variety of goals (e.g., a productivity goal, a profitability goal, a composition supply goal, and an intermediate or final contour goal). The maps, models, and/or excavation plans are then uploaded into excavation and transport machines, and used to direct operations at the raining area.

As the machines move about the mining area, the movements of the machines and the loads carried by the machines can be tracked (e.g., via GPS or local tracking systems, and payload monitoring systems). In this way, material that is being moved by the machines can be identified based on the location in the map or model from which it was removed. In addition, the map and/or model can be updated based on the type and amount of material removed from a particular location in the mining area and deposited at another location. Map-based identification of excavated material, in conjunction with tracking of the identified material as it is moved, is known as material tagging. An exemplary material tagging system is disclosed in U.S. Pat. No. 5,850,341 of Fournier et al. that issued on Dec. 15, 1998.

Accuracy in material tagging can be important. In particular, errors in excavation of ore seams can be costly, and providing an incorrect supply of material to a customer can be problematic. For example, if time is spent excavating material that is not useful to the mine owner or material that has a low value, the mine may not be profitable. In another example, providing the incorrect material to a customer could result in integrity or quality problems in projects completed by the customers (e.g., in roadway projects, bridge projects, building projects, etc). Errors can be introduced throughout the material tagging process, and current material tagging systems may not have a way to check the accuracy of the process or to seamlessly accommodate errors in the process when they are discovered.

The disclosed system is directed to overcoming one or more of the problems set forth above and/or other problems of the prior art.

SUMMARY

In one aspect, the present disclosure is directed to a material tagging system for use with an excavation machine having a work tool. The material tagging system may include a locating device positioned onboard the excavation machine and configured to generate a first signal indicative of a location of the excavation machine at a worksite, and a communication device positioned onboard the excavation machine. The material tagging system may also include at least one of an operator input device and a sensor configured to generate a second signal indicative of an identity of material in the work tool, and a controller in communication with the locating device, the communication device, and the at least one of the operator input device and the sensor. The controller may be configured to receive an electronic map of the worksite predicting locations of different types of material, and to make a comparison of the identity of the material corresponding to the second signal with a type of material predicted by the electronic map to be at a location where the first signal indicates the excavation machine was located when the material was loaded into the work tool. The controller may further be configured to selectively generate and communicate offboard the excavation machine an error flag based on the comparison.

In another aspect, the present disclosure is directed to another material tagging system for use with an excavation machine having a work tool. This material tagging system may include a locating device positioned onboard the excavation machine and configured to generate a first signal indicative of a location of the excavation machine at a worksite, and a communication device positioned onboard the excavation machine. The material tagging system may also include at least one of an operator input device and a sensor configured to generate a second signal indicative of an identity of material in the work tool, and a controller in communication with the locating device, the communication device, and the at least one of the operator input device and the sensor. The controller may be configured to receive an electronic map of the worksite predicting locations of different types of material, and to make a comparison of the identity of the material corresponding to the second signal with a type of material predicted by the electronic map to be at a location where the first signal indicates the excavation machine was located when the material was loaded into the work tool. The controller may be further configured to selectively generate and communicate an error flag to a back office at the worksite based on the comparison, and to set up an avoidance zone in the electronic map based on a deviation between the identity of the material in the work tool and the type of material predicted to be at the location where the first signal indicates the excavation machine was located when the material was loaded into the work tool.

In yet another aspect, the present disclosure is directed to a method of managing material at a worksite. The method may include generating a first signal indicative of a location of an excavation machine at a worksite, and receiving input indicative of an identity of material in a work tool of the excavation machine. The method may further include receiving an electronic map of the worksite predicting locations of different types of material, and making a comparison of the identity of the material in the work tool with a type of material predicted by the electronic map to be at a location where the first signal indicates the excavation machine was located when the material was loaded into the work tool. The method may additionally include selectively generating and communicating offboard the excavation machine an error flag based on the comparison.

DETAILED DESCRIPTION

Figure 1:
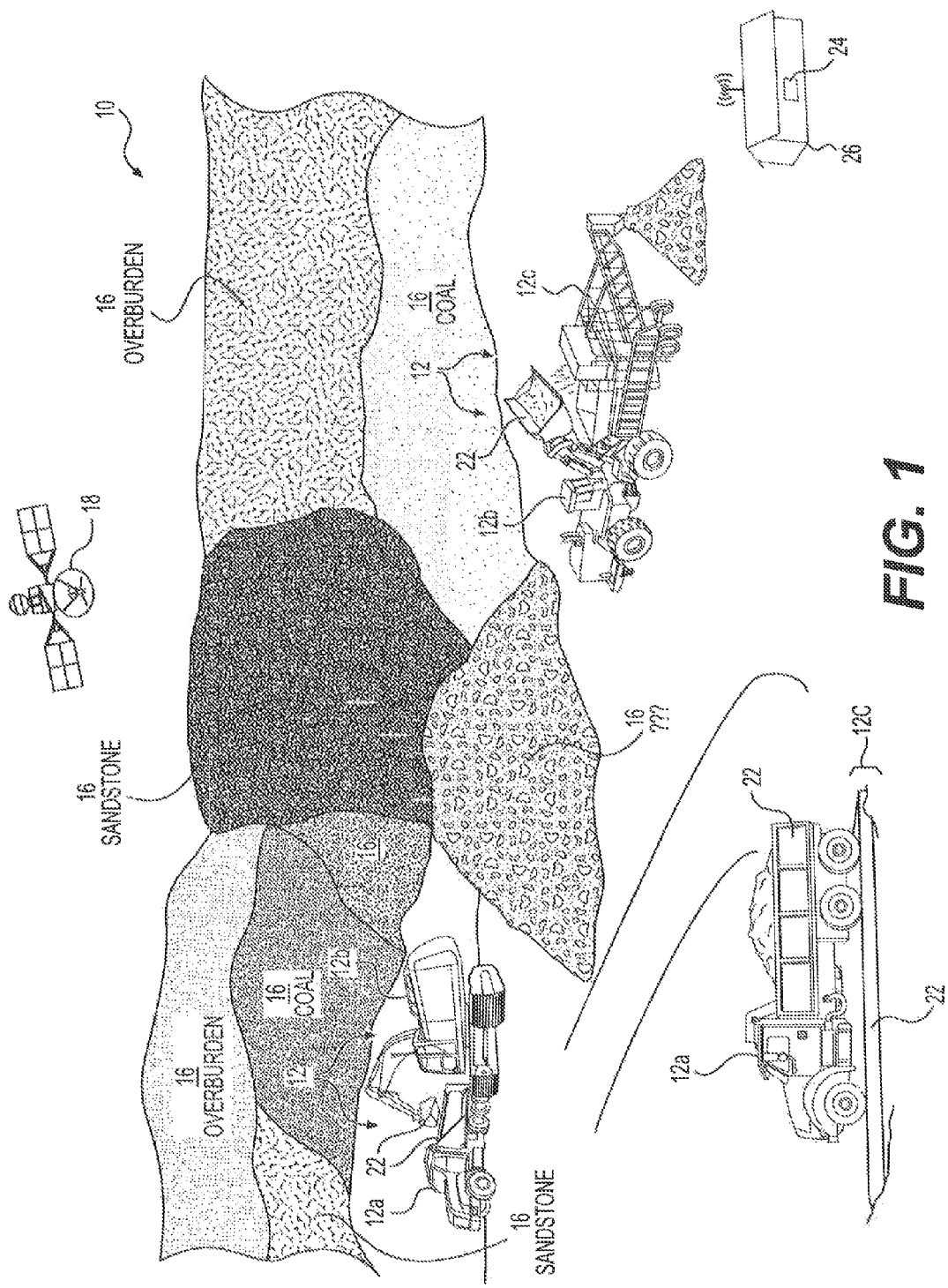
FIG. 1 is an isometric illustration of an exemplary disclosed worksite.

FIG. 1 illustrates a worksite 10 and exemplary excavation machines 12 performing tasks at worksite 10. Worksite 10 may include, for example, a mine site, a landfill, a quarry, a construction site, or any other type of worksite having terrain traversable by machines 12. The tasks being performed by machines 12 may be associated with altering the geography at worksite 10, and may include a dozing operation, a bailing operation, a hauling operation, a grading operation, a leveling operation, a plowing operation, a drilling operation, a crushing operation, or any other type of operation. As machines 12 operate at worksite 10, the shapes, dimensions, and general surface contours of the terrain may change.

Three exemplary types of excavation machines 12 are illustrated in FIG. 1, including a transport machine 12a, a load machine 12b, and a processing machine 12c. Transport machines 12a may be any type of transport machines known in the art, for example on-highway haul machines or off-highway mining or articulated haul machines. Load machines 12b may be any type of load machines known in the art, for example wheel loaders, excavators, shovels, or draglines. Processing machines 12c may be any type of processing machines known in the art, for example, crushers, mixers, conveyors, scales, compactors, motor graders, dozers, tractors, etc. In the illustration of FIG. 1, transport, load, and processing machines 12a, 12b, 12c are shown as cooperating during an excavation process, in which load machines 12b dig earthen material and dump the material into waiting transport machines 12a for transportation to processing machines 12c.

In some embodiments, excavation machines 12 are manned machines. In other embodiments, some or all of excavation machines 12 are remotely controlled, autonomously controlled, or semi-autonomously controlled. Regardless of how excavation machines 12 are controlled, control of excavation machines 12 may be enhanced via reference to an electronic map or model (e.g., 2-D or 3-D virtual model) of worksite 10. These electronic representations may depict surface contours of worksite 10, as well as predicted locations (e.g., boundaries or zones) of ore deposits 16 within worksite 10. Different ore deposits 16 may be shown together in the same map, and categorized or separated from each other based on any criteria known in the art. For example, ore deposits 16 may categorized as overburden, coal, shale, sandstone, etc., based on type, size, quality, concentration, value, accessibility, retrieval cost, etc. Ore deposits 16 may be shown in the map or model in different ways based on the selected category. Data used to determine the locations, boundaries, and categories may be obtained through any manner, for example via core sampling, aerial photography, and/or surveying.

Other information may also be represented within the electronic map, if desired. For example, as excavation machines 12 move about worksite 10, a satellite 18 or other tracking device may communicate with an onboard controller 20 (shown only in FIG. 2) to monitor the movements of excavation machines 12 and the changes made to worksite 10 by work tools 22 attached to excavation machines 12. As will be explained in more detail below, onboard controller 20 or a separate offboard controller 24 (e.g., a controller 24 located in a back office 26 or other service facility at worksite 10) may then manage and update the electronic map of worksite 10 based on these movements and changes.

Both of onboard and offboard controllers 20, 24 may include means for monitoring, recording, storing, indexing, processing, communicating and/or controlling other onboard and/or offboard devices. These means may include, for example, a memory, one or more data storage devices, a central processing unit, or any other components that may be used to run the disclosed application. Furthermore, although aspects of the present disclosure may be described generally as being stored in memory, one skilled in the art will appreciate that these aspects can be stored on or read from different types of computer program products or computer-readable media such as computer chips and secondary storage devices, including hard disks, floppy disks, optical media, CD-ROM, or other forms of RAM or ROM.

Figure 2:
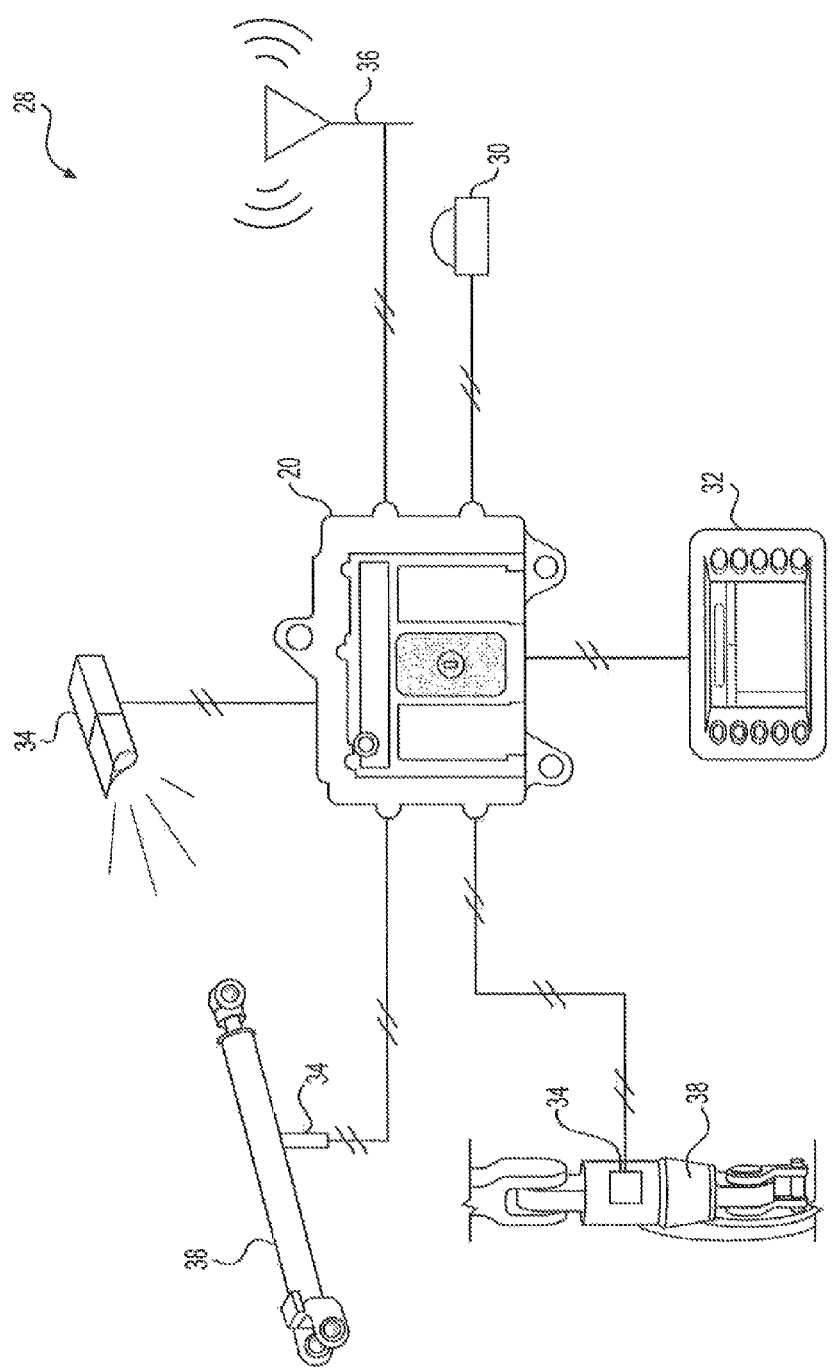
FIG. 2 is a diagrammatic illustration of an exemplary disclosed material tagging system that may be used at the worksite of FIG. 1.

As shown in FIG. 2, onboard controller 20 may form a portion of a material tagging system ("system") 28 that is configured to track movement, of material at worksite 10 by machines 12. In addition to onboard controller 20, system 28 may also include a locating device 30, and at least one of a manual input device 32 and a sensor 34 mounted onboard each machine 12. In some embodiments, system 28 includes both manual input device 32 and one or more sensors 34. Onboard controller 20 may be in communication with each of these other components and/or with offboard controller 24 at back office 26 (e.g., via a communication device 36), and configured to determine, based on signals from these components and based on other known information stored in memory, the location of each machine 12, the surface contours of worksite 10 under each machine 12, and characteristics and locations of material being moved by each machine 12.

Locating device 30 may be configured to generate signals indicative of a geographical position and/or orientation of machine 12 relative to a local reference point, a coordinate system associated with worksite 10, a coordinate system associated with Earth, or any other type of 2-D or 3-D coordinate system. For example, locating device 30 may embody an electronic receiver configured to communicate with satellites 18 (referring to FIG. 1), or a local radio or laser transmitting system used to determine a relative geographical location of itself. Locating device 30 may receive and analyze high-frequency, low-power radio or laser signals from multiple locations to triangulate a relative 3-D geographical position and orientation. In some embodiments, locating device 30 may also be configured to determine a location and/or orientation of a particular part of machine 12, for example of work tool 22 (shown only in FIG. 1). Based on the signals generated by locating device 30 and based on known kinematics of machine 12, onboard controller 20 may be able to determine in real time the position, heading, travel speed, acceleration, and orientation of machine 12 and work tool 22. This information may then be used by onboard and/or offboard controllers 20, 24 to update the locations of machines 12 in the electronic map of worksite 10, as well as origination and final resting locations of material moved by work tools 22.

Input device 32 may provide a way for an operator of machine 12 to input information regarding observances made while traveling around worksite 10. For example, the operator may be able to enter a type of material observed at a particular location, a type of material excavated by or received by machine 12, a property of the material (e.g., a moisture level, a hardness, a viscosity, etc.), or other information about the material engaged by, excavated by, loaded into, or processed by machine 12. The information may be input an any number of ways, for example via a touch screen interface, via one or more buttons, via a keyboard, via speech recognition, or in another manner known in the art. In some embodiments, in addition to receiving manual input from an operator, input device 32 may also be capable of displaying information, for example the electronic map or the 3-D model of worksite 10, instructions from back office 26, payload information, cycle count, etc.

Sensors 34 may be configured to monitor parameters associated with the material being moved by machine 12 (e.g., moved by work tool 22) and to generate corresponding signals indicative thereof. Each of these sensors 34 may be any type of device known in the art, and located anywhere on excavation machines 12. In one example, sensors 34 may embody any one or more of a load cell, a force gauge, a pressure sensor, or another type of load detector associated directly with work tool 22 or associated with an actuator 38 that is connected to move work tool 22. In this example, the signals generated by sensor(s) 34 may correspond with strain on work tool 22 and/or with a force applied to work tool 22 by actuator 38. Alternatively, one or more sensors 34 may be associated with a power source of machine 12 or a drivetrain, and configured to generate signals indicative of an amount of power used to push machine 12 against the material. Other types of sensors 34 (e.g., cameras, spectrometers, IR sensors, RADAR sensors, LIDAR sensors, etc.) may also be utilized to determine the characteristics of the material moved by machine 12. These signals may be communicated to onboard and/or offboard controllers 20, 24, and the appropriate controller may use the signals to identify the material as a particular type of any number of different possible types of material expected to be encountered by machines 12 at worksite 10.

Onboard controller 20 may be configured to manage communications between other onboard components and offboard controller 24 located at back office 26. For example, onboard controller 20 may receive signals from locating device 30, input device 32, and sensors 34, and correlate the signals, filter the signals, buffer the signals, record the signals, or otherwise condition the signals before directing the signals offboard via communication device 36. In some embodiments, onboard controller 20 may have additional functionality, for example autonomous or semi-autonomous control functionality over machines 12, if desired.

Communication device 36 may be configured to facilitate communication between onboard controllers 20 and offboard controller 24. Communication device 36 may include hardware and/or software that enable the sending and/or receiving of data messages through a communications link. The communications link may include satellite, cellular, infrared, radio, and any other type of wireless communications. Alternatively, the communications link may include electrical, optical, or any other type of wired communications, if desired. In one embodiment, onboard controller 20 may be omitted, and offboard controller 24 may communicate directly with locating device 30, input device 32, and/or sensors 34 via communication device 36, if desired. Alternatively, onboard controller 20 may be configured to simply broadcast information regarding the material in work tool 22 and/or the location of machine 12, and the onboard controllers 20 of other machines 12 may relay the broadcast information until it is received by offboard controller 24. Other means of communication may also be possible.

Figure 3:
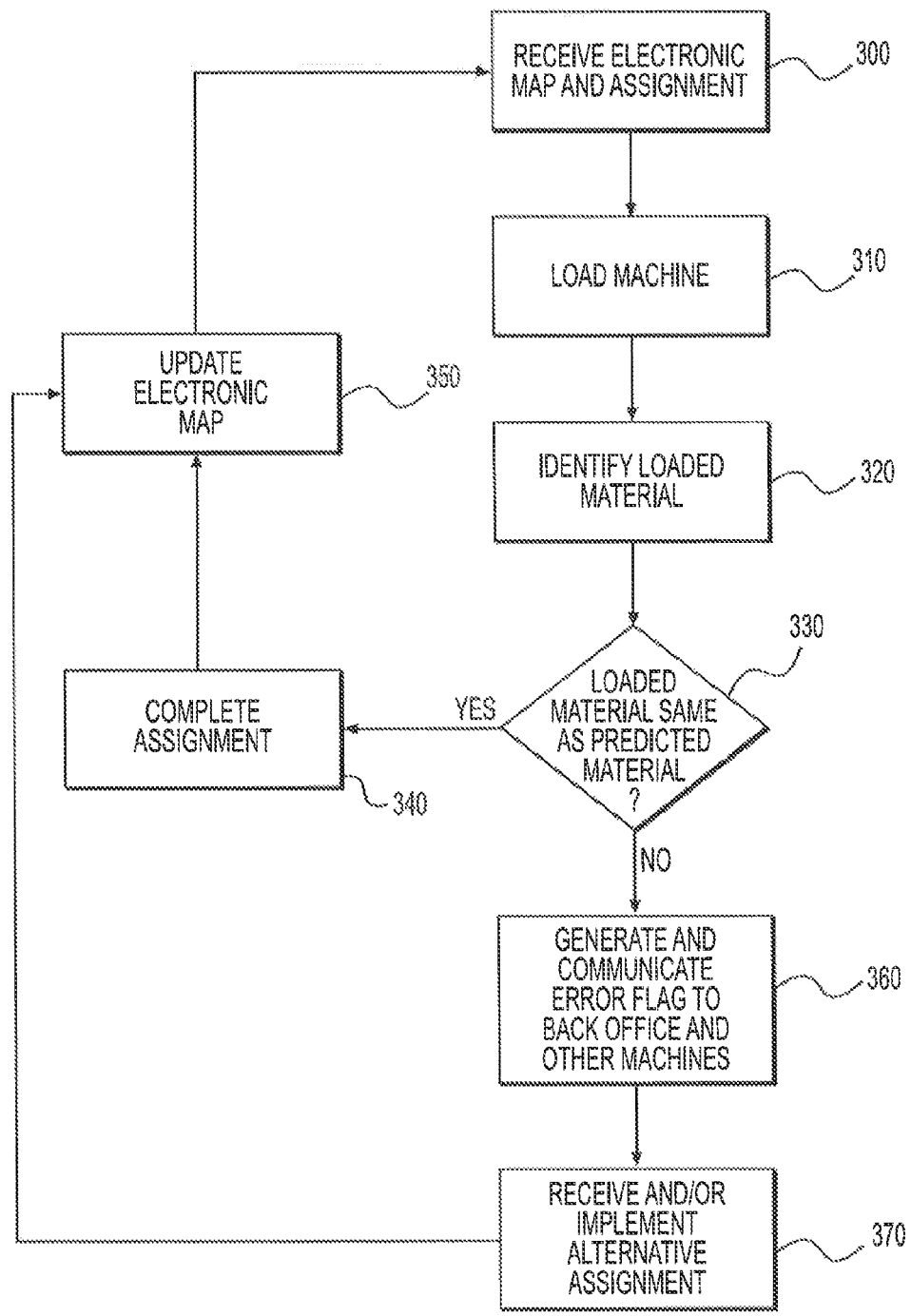
FIG. 3 is a flowchart depicting an exemplary disclosed method that may be performed by the material tagging system of FIG. 2.

Onboard and/or offboard controllers 20, 24, based on the information received from onboard machines 12, may be configured to determine if the material inside, moved by, processed by, or otherwise supported by work tool 22 is the same material predicted by the electronic map of worksite 10 to be at a particular location for alternatively if the received material is the same as or has the properties originally requested for a particular project), and to respond accordingly. This process is illustrated in FIG. 3, and will be explained in more detail in the following section.

INDUSTRIAL APPLICABILITY

The disclosed system 28 may be applicable to any machine and worksite application where accurate material tagging is desirable. The disclosed system 28 may provide a way to track specific types of material at worksite 10, and to ensure accuracy in the tracking. Specifically, system 28 may allow for identity confirmation of material predicted to be at particular locations within worksite 10 as it is being excavated by machines 12. This confirmation may improve worksite efficiencies and profitability, as well as improving the quality and integrity of customer projects that use the material. Operation of system 28 will now be described with reference to FIG. 3.

At startup of a typical workshift, onboard controller 20 of each machine 12 may receive the most updated version of the electronic map of worksite 10. In some embodiments, this map may include the types, shapes, and/or amounts of materials found is specifics locations at worksite 10. In other embodiments, the map may additional or alternatively include specifications of worksite 10, such as desired compaction levels, moisture levels, etc. Each onboard controller 20 may also receive an assignment for the given workshift that is, at least in part, based on the locations and/or orientations of the different ore deposits 16 represented in the electronic map (Step 300). For example, a particular excavation machine 12b (e.g., the hydraulic excavator shown in the upper left corner of FIG. 1) may be dispatched to a particular 3-D coordinate at worksite 10 and assigned to load a certain type (e.g., coal) and amount of ore from a designated deposit $16_{coal}$ into transport machine 12a. Excavation machine 12b, under the control of a human operator and guidance of onboard controller 20 or under the autonomous or semi-autonomous control of onboard controller 20, may then move to the assigned coordinates and begin loading material from deposit $16_{coal}$ into transport machine 12a (Step 310).

As the excavation process advances, the material at the assigned coordinates (e.g., in deposit $16_{coal}$) may be identified (Step 320). The material may be identified in any number of ways. For example, the operator of excavation machine 12b and/or transport machine 12a may visually determine what the identity is of the material at deposit $16_{coal}$. In particular, the operator may be able to see the ore seam in an excavation face at worksite 10 and/or see the material as it is being scooped up by work tool 22 of excavation machine 12b or loaded by excavation machine 12b into work tool 22 of transport machine 12a. The operator may recognize the appearance of the material and thereby identify the material. Alternatively or additionally, the operator may be able to perceive a parameter of the material (e.g., a hardness, a moisture content, a viscosity, a shape, etc.) as it is being excavated or loaded and thereby identify the material. The operator may then input the observations and/or identity of the material via input device 32.

In another example, the material may be automatically identified based on the operator input and/or input received from sensors 34. In particular, based on entered material characteristics, sensed parameters (e.g., weight, moisture content, hardness), and/or recorded images of the material, onboard and/or offboard controllers 20, 24 may reference this information with known machine specifications (e.g., work tool volume) with lookup tables stored in memory to automatically determine the identity of the material.

Onboard and/or offboard controllers 20, 24 may then make a comparison of the determined identity of the material with an identity of material predicted by and shown in the electronic map of worksite 10 (Step 330). If the determined identity is the same as the predicted identity, the excavation process is proceeding as planned and machines 12 may complete their assigned tasks without disruption (Step 340).

As the excavation process advances normally, onboard and/or offboard controllers 20, 24 may update the electronic map (Step 350). In particular, the map may be adjusted to show where material was taken from and, based on its excavation location, the material may be tagged as the confirmed type of material. In other words, as long as the determined identity is confirmed to be the same as the predicted identity, all material removed by machines 12 may be electronically labeled as the corresponding type of material. And the location from which the material was excavated may become smaller in the electronic map as the material is being removed, based on tracked movements of machines 12 (particularly tracked movements of work tool 22). In addition, as machines 12 transport the material to other locations at worksite 10, the other locations may become larger in the electronic map. The increase in size at these other locations may be encoded in the electronic map with the confirmed identification of the material. For example, if coal is confirmed to be excavated from ore deposit $16_{coal}$, deposit $16_{coal}$ may shrink in size by an amount proportional to the amount of material removed. As this same material is then deposited at another location, that location may grow by the same amount and the growth may be identified in the electronic map as being coal. Control may return from step 350 to step 300.

It should be noted that the identity comparison of Step 320 may be performed by any operator and any machine at worksite 10, and confirmed any number of times. For example, the operator of excavation machine 12b may visually confirm the identity of the material as the material is being excavated from deposit $16_{coal}$, while controller 20 (via sensors 34) also automatically confirms the identity of the material (e.g., via a captured image). In addition or alternatively, the operator and/or controller 20 of transport machine 12a could confirm the identity of the material as the material is being received. Further, the identity of the material could alternatively and/or additionally be confirmed by a similar controller 20 associated with any one of processing machines 12c (e.g., by the scale based on a density determined as a function of sensed weight and known work tool volume, or by the crusher based on a sensed hardness), or by another operator or machine, if desired.

At step 340, however, when a comparison shows a difference between the determined identity and the predicted identity, onboard controller 20 may selectively generate an error flag and communicate the error flag to back office 26 and to other machines 12 at worksite 10 (Step 360). In one example, the error flag may be directly communicated between onboard and offboard controllers 20, 24 via communication device 36. In another example, the error flag may be communicated via a peer-to-peer network. In other words, controller 20 of one machine 12 may broadcast the error flag within a surrounding region, and other machines 12 within that region may relay the broadcast until the error flag is received by offboard controller 24.

Many different actions may be taken in response to generation of the error flag. For example, controller 20 onboard the machine 12 that determined the identity difference may receive and/or implement an alternative assignment (Step 370). In one embodiment, the alternative assignment may be received from offboard controller 24 (e.g., from back office 26 and/or another machine 12) as a means to accommodate the identity deviation. In another embodiment, the alternative assignment may be preprogrammed into onboard controller 20 and automatically implemented in response to generation of the error flag. In yet another embodiment, onboard controller 20 (or alternatively offboard controller 24) may need to run an excavation simulation program using the new material identification in order to rearrange task assignments. The alternative assignment could include, for example, designating the corresponding location (e.g., deposit $16_{coal}$) as an avoidance zone ($16_{???}$) having some ambiguity regarding the identity of its contents. The avoidance zone may be a zone that should be completely avoided by all machines 12, a zone in which excavation machines 12b should not dig (i.e., a no-dig zone), or just a zone in which material properties did not meet expectations. In another example, the alternative assignment could include transportation of excavated material from the ore deposit in question to a different end location. In yet another example, the assignment may include pausing excavation activities until an additional survey can be completed or until manual inspection of the location and/or surrounding locations can be completed.

It is contemplated that the alternative assignment could be different depending on when the difference between the determined and predicted identities is established. For example, if the difference is determined when the material is being excavated, the alternative assignment may be for excavation machine 12a to move to a different location and continue excavation activities. But if the difference is determined when the material is being transported, the alternative assignment may include dumping of the material at a different location. And if the difference is determined after the material is dumped and/or is being processed, the alternative assignment may include altering the processing of the material (e.g., crushing the material to a different size or mixing the material differently). The electronic model may then be updated during completion of the alternative assignment. That is, control may proceed from step 370 to step 350.

It is contemplated that, at step 350 during map updating, in addition to updating the map to reflect a deviation between determined identity and expected identity of an excavated material, the map could also be updated to reflect an outcome of a processing operation. For example, if a road was built with incorrect material and did not achieve a required compaction level after a stipulated compaction process was completed, that road may also be marked on the electronic map and flagged as not meeting required specifications. This may allow for replacement of that section of road, for additional processing steps to be completed, or for other actions to be taken.

In a further embodiment, the map could additionally or alternatively reflect a problem associated with the processing operation itself. Returning to the road building example from above, it might be possible for the correct road base material to have been delivered to a first processing machine 12c (e.g., to an asphalt mixing machine or factory), but for the first processing machine 12c to have incorrectly mixed the material (e.g., added in incorrect amount of bitumen) before delivery to a second processing machine 12c (e.g., to the compactor). In this situation, in addition to or instead of flagging the location in the map from which the road material was excavated as an avoidance zone, the first processing machine 12c itself could also be flagged as a potential cause of the deviation.

It will be apparent to those skilled in the art that various modifications and variations can be made to the disclosed system. Other embodiments will be apparent to those skilled in the art from consideration of the specification and practice of the disclosed system. It is intended that the specification and examples be considered as exemplary only, with a true scope being indicated by the following claims and their equivalents.

What is claimed is:

1. A material tagging system for use with an excavation machine having a work tool, the material tagging system comprising:
   a locating device positioned onboard the excavation machine and configured to generate a first signal indicative of a location of the excavation machine at a worksite;
   a communication device positioned onboard the excavation machine;
   at least one of an operator input device and a sensor configured to generate a second signal indicative of an identity of material in the work tool; and
   a controller in communication with the locating device, the communication device, and the at least one of the operator input device and the sensor, the controller being configured to:
      receive an electronic map of the worksite predicting locations of different types of material;
      make a comparison of the identity of the material corresponding to the second signal with a type of material predicted by the electronic map to be at a location where the first signal indicates the excavation machine was located when the material was loaded into the work tool;
      selectively generate and communicate offboard the excavation machine an error flag based on the comparison; and
      automatically implement an alternative excavation assignment based on a deviation between the identity of the material in the work tool and the type of material predicted to be at the location where the first signal indicates the excavation machine was located when the material was loaded into the work tool.

2. The material tagging system of claim 1, wherein the controller is configured to broadcast the error flag to other machines operating at the worksite.

3. The material tagging system of claim 1, wherein the controller is further configured to:
   receive error flags broadcast from other machines operating at the worksite; and
   relay received error flags to the other machines operating at the worksite.

4. The material tagging system of claim 3, wherein the controller is further configured to set up an avoidance zone in the electronic map based on error flags received from other machines.

5. The material tagging system of claim 1, wherein the controller is further configured to set up an avoidance zone in the electronic map based on the deviation between the identity of the material in the work tool and the type of material predicted to be at the location where the first signal indicates the excavation machine was located when the material was loaded into the work tool.

6. The material tagging system of claim 1, wherein the controller is configured to:
   communicate the error flag to a back office; and
   receive instruction from the back office regarding how to accommodate the deviation between the identity of the material in the work tool and the type of material predicted to be at the location where the first signal indicates the excavation machine was located when the material was loaded into the work tool.

7. The material tagging system of claim 1, wherein the controller is configured to selectively run an excavation simulation program based on the deviation between the identity of the material in the work tool and the type of material predicted to be at the location where the first signal indicates the excavation machine was located when the material was loaded into the work tool.

8. The material tagging system of claim 1, wherein the controller is further configured to update the electronic map based on the first and second signals.

9. The material tagging system of claim 1, wherein:
   the at least one of the operator input device and the sensor includes a load sensor, and the second signal is associated with a weight of the material in the work tool; and
   the controller is configured to determine the identity of the material by calculating a density of the material as a function of the weight and a known volume of the work tool, and referencing the density with a lookup table stored in memory.

10. The material tagging system of claim 1, wherein the at least one of the operator input device and the sensor includes a spectrometer.

11. The material tagging system of claim 1, wherein the at least one of the operator input device and the sensor includes a camera.

12. The material tagging system of claim 1, wherein the at least one of the operator input device and the sensor includes a device configured to receive from an operator of the excavation machine a manually entered observation corresponding to the identity of the material.

13. The material tagging system of claim 1, wherein the at least one of the operator input device and the sensor includes both an operator input device and a sensor, each of the operator input device and the sensor being configured to generate signals indicative of the identity of the material in the work tool.

14. The material tagging system of claim 1, wherein the at least one of the operator input device and the sensor is located onboard a transport machine receiving the material from the excavation machine.

15. The material tagging system of claim 1, wherein:
   the at least one of the operator input device and the sensor is located onboard a processing machine configured to process material received from the excavation machine; and
   the second signal is indicative of a material parameter exhibited during processing of the material.

16. A material tagging system for use with an excavation machine having a work tool, the material tagging system comprising:
   a locating device positioned onboard the excavation machine and configured to generate a first signal indicative of a location of the excavation machine at a worksite;

at least one of an operator input device and a sensor configured to generate a second signal indicative of an identity of material in the work tool; and a controller in communication with the locating device and the at least one of the operator input device and the sensor, the controller being configured to:
- make a comparison of the identity of the material corresponding to the second signal with a type of material predicted to be at a location where the first signal indicates the excavation machine was located when the material was loaded into the work tool;
- selectively generate and communicate an error flag based on the comparison; and
- automatically implement an alternative excavation assignment based on a deviation between the identity of the material in the work tool and the type of material predicted to be at the location where the first signal indicates the excavation machine was located when the material was loaded into the work tool.

17. A method for managing material at a worksite, the method comprising:
- generating a first signal indicative of a location of an excavation machine at a worksite;
- receiving input indicative of an identity of material in a work tool of the excavation machine;
- receiving an electronic map of the worksite predicting locations of different types of material;
- making a comparison of the identity of the material in the work tool with a type of material predicted by the electronic map to be at a location where the first signal indicates the excavation machine was located when the material was loaded into the work tool;
- selectively generating and communicating offboard the excavation machine an error flag based on the comparison; and
- automatically implementing an alternative excavation assignment based on a deviation between the identity of the material in the work tool and the type of material predicted to be at the location where the first signal indicates the excavation machine was located when the material was loaded into the work tool.

18. The method of claim 17, further including setting up an avoidance zone in the electronic map based on the deviation between the identity of the material in the work tool and the type of material predicted to be at the location where the first signal indicates the excavation machine was located when the material was loaded into the work tool.

19. The method of claim 17, wherein:
- communicating the error flag offboard the excavation machine includes communicating the error flag to a back office; and
- the method further includes receiving instruction from the back office regarding how to accommodate a deviation between the identity of the material in the work tool and the type of material predicted to be at the location where the first signal indicates the excavation machine was located when the material was loaded into the work tool.

20. The material tagging system of claim 16, wherein the type of material is predicted based on an electronic map, wherein the controller is configured to:
- selectively run an excavation simulation program based on the deviation between the identity of the material in the work tool and the type of material predicted to be at the location where the first signal indicates the excavation machine was located when the material was loaded into the work tool; and
- set up an avoidance zone in the electronic map based on the deviation between the identity of the material in the work tool and the type of material predicted to be at the location where the first signal indicates the excavation machine was located when the material was loaded into the work tool.

* * * * *